(12) United States Patent
Beise (10) Patent No.: US 10,980,489 B2
(45) Date of Patent: Apr. 20, 2021

(54) METHOD AND DEVICE FOR QUANTIFYING A RESPIRATORY SINUS ARRHYTHMIA AND USE OF SAID TYPE OF METHOD OR SAID TYPE OF DEVICE

(71) Applicant: BioSign Medical UG, Ottenhofen (DE)

(72) Inventor: Reinhard Beise, Ottenhofen (DE)

(73) Assignee: BioSign Medical UG, Ottenhofen (DE)

( * ) Notice: Subject to any disclaimer, the term of this patent is extended or adjusted under 35 U.S.C. 154(b) by 342 days.

(21) Appl. No.: 15/762,381

(22) PCT Filed: Sep. 22, 2016

(86) PCT No.: PCT/DE2016/100445
§ 371 (c)(1),
(2) Date: Mar. 22, 2018

(87) PCT Pub. No.: WO2017/050321
PCT Pub. Date: Mar. 30, 2017

(65) Prior Publication Data
US 2018/0263567 A1 Sep. 20, 2018

Related U.S. Application Data

(60) Provisional application No. 62/243,356, filed on Oct. 19, 2015.

(30) Foreign Application Priority Data

Sep. 23, 2015 (DE) ..................... 10 2015 116 044.7

(51) Int. Cl.
| | | |
|---|---|---|
| A61B 5/00 | (2006.01) | |
| A61B 5/024 | (2006.01) | |
| A61B 5/0205 | (2006.01) | |
| A61B 5/08 | (2006.01) | |

(52) U.S. Cl.
CPC .......... *A61B 5/7225* (2013.01); *A61B 5/0205* (2013.01); *A61B 5/02405* (2013.01);
(Continued)

(58) Field of Classification Search
None
See application file for complete search history.

(56) References Cited

U.S. PATENT DOCUMENTS

| | | |
|---|---|---|
| 6,358,201 B1 | 3/2002 | Childre et al. |
| 7,163,512 B1 | 1/2007 | Childre et al. |
| (Continued) | | |

FOREIGN PATENT DOCUMENTS

| | | |
|---|---|---|
| DE | 600 32 581 T2 | 10/2007 |
| DE | 10 2006 039 957 A1 | 3/2008 |
| (Continued) | | |

OTHER PUBLICATIONS

Hoshi et al. Poincaré plot indexes of heart rate variability: Relationships with other nonlinear variables; Autonomic Neuroscience: Basic and Clinical 177 (2013) 271-27 (Year: 2013).*

(Continued)

*Primary Examiner* — Kaylee R Wilson
*Assistant Examiner* — Jay B Shah
(74) *Attorney, Agent, or Firm* — Collard & Roe, P.C.

(57) ABSTRACT

In a method and a device for quantification of a respiratory sinus arrhythmia, a heart-rate curve is measured first and then the time elapsed between two heartbeats is determined and quantified by an analysis in the phase domain. A more informative quantification is obtained when suitable coefficients are used or the heart-rate curve is interpolated and/or detrended for the quantification.

10 Claims, 9 Drawing Sheets

(52) U.S. Cl.
CPC ............ *A61B 5/4035* (2013.01); *A61B 5/486* (2013.01); *A61B 5/7278* (2013.01); *A61B 5/742* (2013.01); *A61B 5/0816* (2013.01)

(56) References Cited

U.S. PATENT DOCUMENTS

| | | | |
|---|---|---|---|
| 7,462,151 | B2 | 12/2008 | Childre et al. |
| 7,860,560 | B2 | 12/2010 | Beise |
| 8,066,637 | B2 | 11/2011 | Childre et al. |
| 8,123,696 | B2 | 2/2012 | Childre et al. |
| 8,467,859 | B2 | 6/2013 | Krauss et al. |
| 2005/0261557 | A1* | 11/2005 | Baker .................. A61B 3/0083 600/300 |
| 2006/0074333 | A1 | 4/2006 | Huiku |
| 2007/0208266 | A1 | 9/2007 | Hadley |
| 2010/0198092 | A1* | 8/2010 | Jimenez-Acquarone .................... A61B 5/02405 600/515 |
| 2011/0144513 | A1 | 6/2011 | Deluz |

FOREIGN PATENT DOCUMENTS

| | | |
|---|---|---|
| DE | 10 2008 030 956 A1 | 4/2009 |
| DE | 10 2011 012 619 A1 | 8/2012 |
| DE | 10 2012 025 183 A1 | 7/2014 |
| EP | 1 156 630 A1 | 11/2001 |
| EP | 1 156 851 B1 | 12/2006 |
| WO | 2008/028912 A2 | 3/2008 |
| WO | 2014/101913 A1 | 7/2014 |

OTHER PUBLICATIONS

Karmakar et al. Novel Feature for Quantifying Temporal Variability of Poincare Plot: A Case Study; Computers in Cardiology 2009; 36:53-56. (Year: 2009).*

De Couck et al., "You may need the vagus nerve to understand pathophysiology and to treat diseases", Clinical Science (2012) 122, Great Britain, pp. 323-328.

Thayer et al., "The relationship of autonomic imbalance, heart rate variability and cardiovascular disease risk factors", International Journal of Cardiology, Elsevier (2009), pp. 1-10.

Heart rate Variability, Standards of measurement, physiological interpretation, and clinical use, Task Force of the European Society of Cardiology and the North American Society of Pacing and Electrophysiology (Membership of the Task Force listed in the Appendix) European Heart Journal (1996), pp. 354-381.

Ahuja et al, "Heart Rate Variability and its Clinical Application for Biofeedback", Proceedings of the 17th IEEE Symposium on Computer-Based Medical Systems(CBMS'04), 2004, pp. 1-4.

International Search Report of PCT/DE2016/100445, dated Feb. 20, 2017.

Tarvainen et al., An Advanced Detrending Method with Application to HRV Analysis, IEEE Transactions on Biomedical Engineering, vol. 49, No. 2, Feb. 2002.

Hsu et al., Poincaré plot indexes of heart rate variability detect dynamic autonomic modulation during general anesthesia induction, Acta Anaesthesiologica Taiwanica 50 (2012) 12-18.

Piskorski et al., Filtering Poincaré plots, Computational Methods in Science and Technology 11 (1), pp. 39-48, (2005).

Guzik et al., Correlations between the Poincaré Plot and Conventional Heart Rate Variability Parameters Assessed during Paced Breathing, The Journal of Physiological Sciences, Mar. 2007, pp. 63-71.

Brennan et al., "Do Existing Measures of Poincare Plot Geometry Reflect Nonlinear Features of Heart Rate Variability?", IEEE Transactions on Biomedical Engineering, vol. 48, No. 11, Nov. 2001, pp. 1342-1347.

* cited by examiner

METHOD AND DEVICE FOR QUANTIFYING A RESPIRATORY SINUS ARRHYTHMIA AND USE OF SAID TYPE OF METHOD OR SAID TYPE OF DEVICE

CROSS REFERENCE TO RELATED APPLICATIONS

This application is the National Stage of PCT/DE2016/100445 filed on Sep. 22, 2016, which claims priority under 35 U.S.C. § 119 of German Application No. 10 2015 116 044.7 filed on Sep. 23, 2015, and under 35 U.S.C. § 119(e) of U.S. Provisional Application Ser. No. 62/243,356 filed on Oct. 19, 2015, the disclosures of all of the above applications are incorporated herein by reference.

The invention relates to a method and to a device for quantification of a respiratory sinus arrhythmia as well as to use of such a method or of such a device.

The fluctuations of heart rate from heartbeat to heartbeat are known as heart-rate variability, abbreviated HRV, or else heart-frequency variability. The HRV can be quantified by appropriate mathematical methods, e.g. by means of the common statistical measure of dispersion known as "standard deviation". The heart-rate variability is manifestation of the continuous adaptation of the heart rate to fluctuating demands in the human organism and therefore permits conclusions on the neurovegetative regulation ability of the human being. In particular, special importance in this context is ascribed to the function of the parasympathetic nervous system with its main nerve (vagus nerve) (Clin Sci (Lond). 2012 April; 122(7):323-8 You may need the vagus nerve to understand pathophysiology and to treat diseases; De Couck M, Mravec B, Gidron Y).

An inadequate function of the parasympathetic system or a predomination of the sympathetic system may manifest itself in a smaller HRV. In serious cases, the pattern of complete absence of heart-rate variability may exist. The relationship between low HRV and increased morbidity and mortality has been frequently confirmed in numerous studies and is now regarded as certain (Int J Cardiol. 2010 May 28; 141(2):122-31. Epub 2009 Nov. 11 The relationship of autonomic imbalance, heart rate variability and cardiovascular disease risk factors; Thayer J F, Yamamoto S S, Brosschot J F).

The determination of the HRV by means of heart-rate analysis at rest and under stimulation is now considered as the most important investigation method in the diagnosis of the autonomic nervous system (Eur Heart J. 1996 March; 17(3):354-81 Heart rate variability. Standards of measurement, physiological Interpretation, and clinical use. Task Force of the European Society of Cardiology and the North American Society of Pacing and Electrophysiology).

Figure 1:
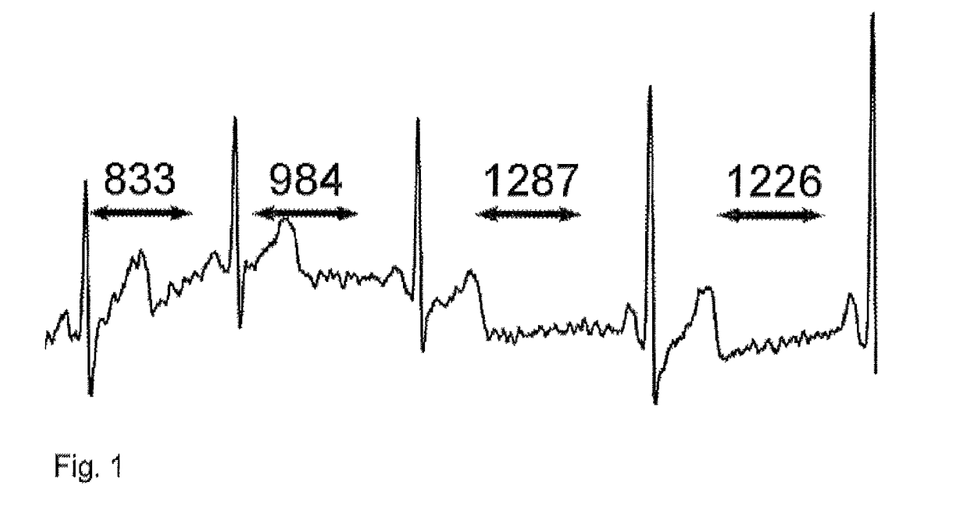
FIG. 1 shows a typical EKG with 4 heartbeats.

The basis of any HRV calculation is the heart-rate curve, which for each heartbeat quantifies the time elapsed since the preceding heartbeat, either as a time interval or as the resulting heart rate, which is expressed as the quotient of 60 divided by the time interval in seconds. The heart-rate curve may be recorded from EKG or pulse curves. Thus FIG. 1 shows a typical EKG with 4 heartbeats, recognizable by the large ascending waves (R-waves). The time elapsed between two R-waves corresponds to the interval between two heartbeats and can be quantified, for example in milliseconds. From this elapsed time, also known as RR interval, the heart rate of a heartbeat is calculated as follows:

Heart rate [bpm]=60000/$RR$ interval [ms]

If the EKG recording is started at instant t=0, for each heartbeat it is possible to indicate the instant of its occurrence, the RR interval and the resulting heart rate, as illustrated by way of example in Table 1.

Figure 2A:
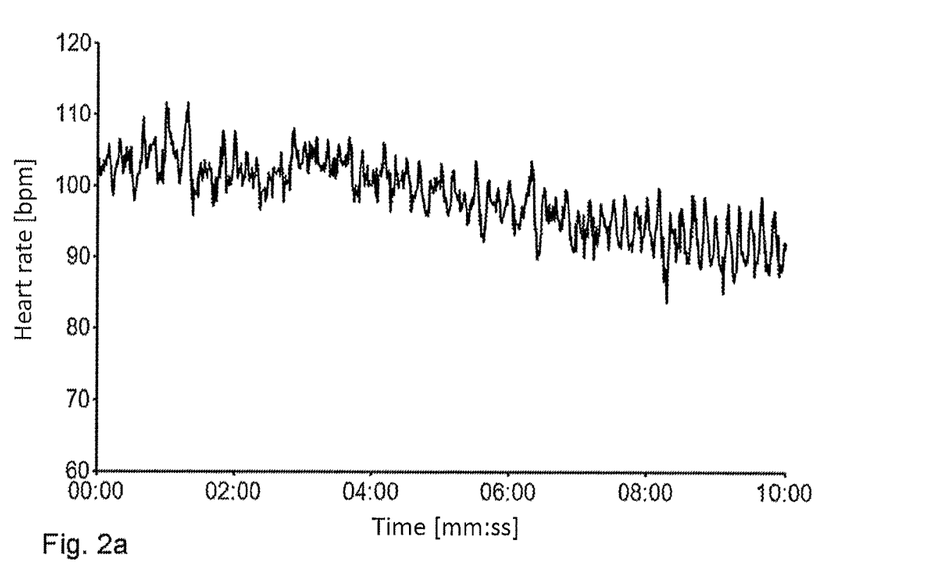
FIG. 2 shows a heart-rate curve before and after a detrending.
Figure 2B:
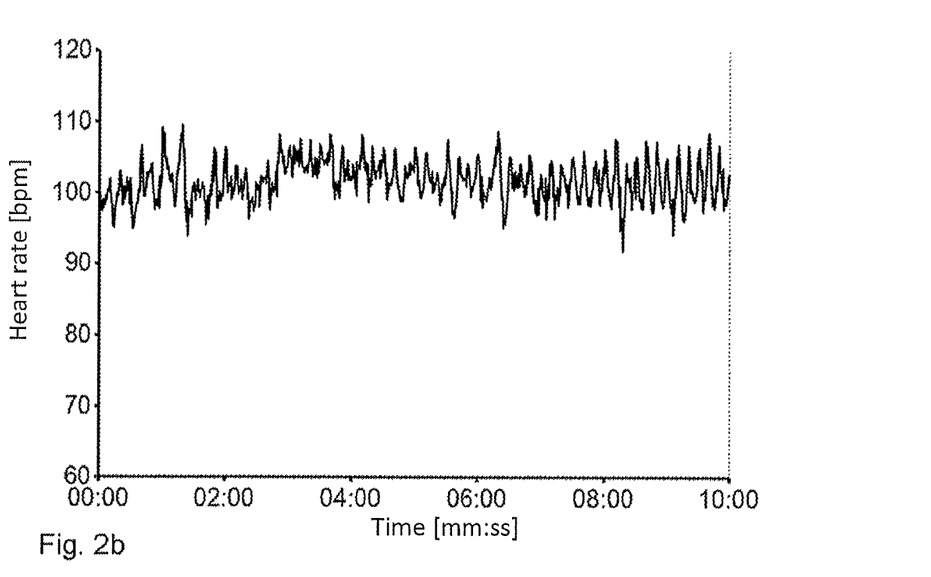
Figure 3A:
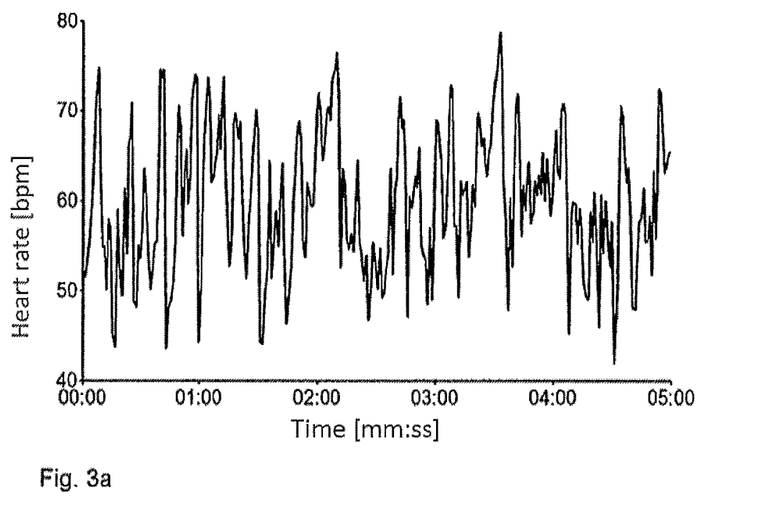
FIG. 3 shows a second heart-rate curve with its fast Fourier transform and an associated Poincaré diagram.

Such a heart-rate list can now be easily converted into a heart-rate diagram, wherein the X-axis is formed by the time column and the Y-axis by the heart-rate column (see FIG. 2). FIG. 3 also shows the typical heart-rate variation of a human being.

Figure 4A:
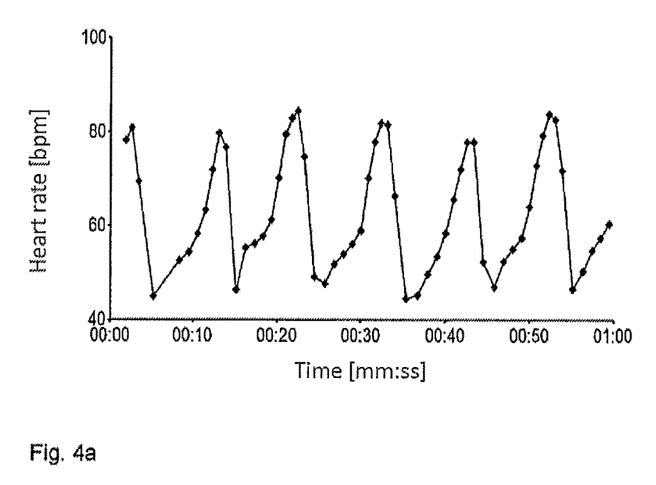
FIG. 4 shows a third heart-rate curve with its fast Fourier transform.
Figure 4B:
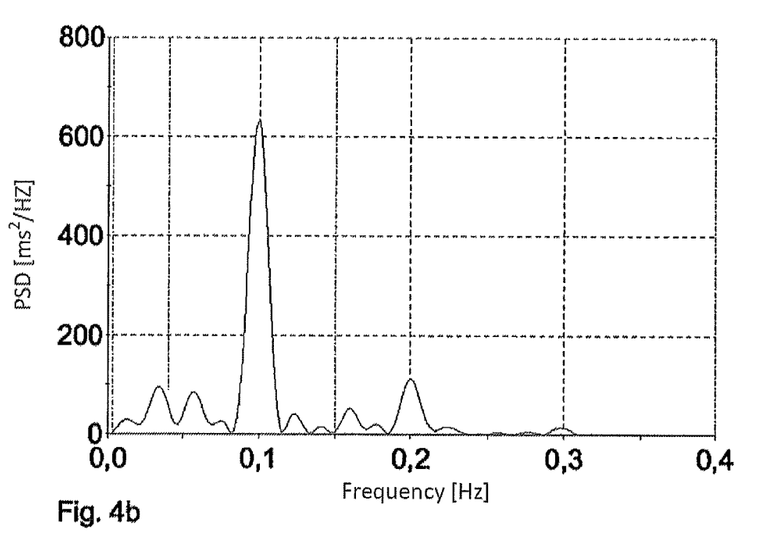

The influence of the parasympathetic nervous system is evident above all in the magnitude of the respiratory sinus arrhythmia (RSA). This is understood as the oscillation of the heart rate synchronously with respiration, wherein the heart rate rises during inspiration and drops again during expiration. FIG. 4a shows an example of a pronounced respiratory sinus arrhythmia, whereas much smaller fluctuations are evident in the examples illustrated in FIGS. 4b and 4c.

The respiratory sinus arrhythmia is mediated exclusively by the parasympathetic system, while the sympathetic system makes no contribution to it. This is based on the speed of the two regulation systems, sympathetic and parasympathetic, of which the parasympathetic system is able to regulate significantly faster than the sympathetic system. This property of the parasympathetic system is put to use in order to differentiate between the activity of the sympathetic system and that of the parasympathetic system, in which the heart-rate variation is subjected to appropriate analysis, for example a spectral analysis, for example, by means of a fast Fourier transform (FFT), as is shown by way of example in FIG. 3b for the heart-rate variation according to FIG. 3a.

Figure 3B:
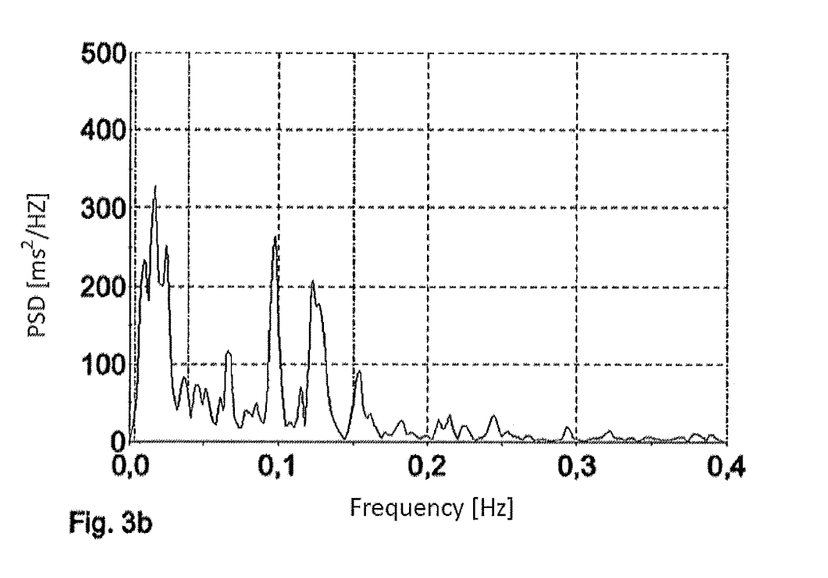

In this connection, the region of the spectral analysis marked as "HF" (high frequency) in FIG. 3b denotes a regulation range of the heart rate that is generated exclusively by the influence of the parasympathetic system (0.15 Hz to 0.4 Hz). The region marked as "LF" (low frequency) comprises a frequency range in which sympathetic and parasympathetic systems overlap (0.04 to 0.15 Hz). The frequency range denoted as "VLF" encompasses very slowly acting influences, such as thermoregulation, for example. Due to the necessary long recording time, the "VLF" range plays no role in short-time HRV analysis and may be disregarded in the further discussion.

It has long been prior art to quantify the different activities of sympathetic and parasympathetic systems by parameters that are obtained by a spectral analysis. For example, in many scientific studies, the LF/HF ratio is used to indicate the balance of sympathetic and parasympathetic systems. This ratio is the integral of the frequency distribution in the LF range over the integral of the frequency curve in the HF range. In this connection, it is assumed that the HF range represents exclusively the parasympathetic system and the LF range approximately reflects the activity of the sympathetic system (Eur Heart J. 1996 March; 17(3):354-81; Heart rate variability. Standards of measurement, physiological Interpretation, and clinical use. Task Force of the European Society of Cardiology and the North American Society of Pacing and Electrophysiology).

A further approach in order to determine the activity of the parasympathetic system is the quantification of the respiratory sinus arrhythmia. In the condition of the respiratory sinus arrhythmia, the synchronization of the rhythms of respiration, blood pressure and heart rate leads to an approximately sinusoidal oscillation of the heart rate (see FIG. 4a), which exhibits a characteristic pattern in the spectral analysis and is marked by a large peak over the respiratory rate (see FIG. 4b). Because of the optimum resonance frequency of the respiratory sinus arrhythmia of approximately 0.1 Hz, the peak of the respiratory sinus arrhythmia practically always lies in the LF (low-frequency) range of the spectral analysis, but is nevertheless the manifestation of parasympathetic activity and is not to be confused with sympathetic activity, which is marked by the absence of a characteristic peak and by a broad distribution of the frequencies occurring in the LF range.

It is therefore possible to determine the amplitude of the respiratory sinus arrhythmia via a spectral analysis. Thus, for example, DE 10 2006 039 957 A1 describes a spectral analysis method for determination of the respiratory sinus arrhythmia, which is based on a ratio of the integral proportion of two frequency ranges, similarly to the LF/HF ratio. EP 1 156 851 B1 and DE 600 32 581 T2 in turn describe a spectral analysis method for determination of the respiratory sinus arrhythmia in which, by means of a peak detection, the frequency of the peak is determined and then an integral that comprises the peak is inserted into the ratio of two integrals, which respectively comprise a range below and above the peak frequency. A practical implementation of the methods mentioned in the two patents are, for example, instruments for performing the so-called HRV biofeedback method. Therein the respiratory sinus arrhythmia of the user is measured in real time and displayed visually by variously colored LEDs. By the so-called biofeedback effect, the user is now able selectively to train his or her respiratory sinus arrhythmia and thus the influence of the health-promoting parasympathetic system. DE 10 2008 030 956 A1 shows an exemplary embodiment of such an instrument.

Because of the needed mathematical methods, such as a Fourier analysis, for example, as disclosed in US 2007/0208266 A1, for example, an FFT analysis, as is disclosed in particular in, for example, EP 1 156 851 B1, WO 2008/028912 A2, U.S. Pat. No. 6,358,201, 7,163,512 B1, 7,462,151 B2, 8,066,637 B2 or 8,123,696 B2, or a wavelet analysis, the determination of the respiratory sinus arrhythmia by means of the spectral analysis according to the prior art necessitates high computing power, as is now entirely possible in the PC sector. US 2006/0074333 A1 also discloses complex computing steps in order to infer the condition of the nervous system from biometric parameters, which are measured. For the realization of simple battery-powered instruments for determination of the respiratory sinus arrhythmia, however, sparingly computation-intensive analysis methods are desirable, because then the use of expensive microprocessors with high current consumption can be avoided. For example, with relatively little computational expense in the time domain, the standard deviation may be used as a prediction of the variance of the corresponding signal (Proceedings of the 17th IEEE Symposium on Computer-Based Medical Systems (CBMS'04) 2004, pages 1 to 4; Raghavan V, Vikas Lath, Ashish Patil Sreejit Pillai).

A suitable mathematical method is, for example, the standard deviation S:

$$S = \sqrt{\frac{\sum_{n=2}^{N}(X_n - X_{mean})^2}{N-1}},$$

where $X_n$ is the respective heart rate, N is the number of heart rates respectively being investigated and $X_{mean}$ is the mean value of the heart rates $X_n$:

$$X_{mean} = \frac{\sum_{n=1}^{N} X_n}{N}.$$

However, this approach has proved to be poorly informative.

Figure 5A:
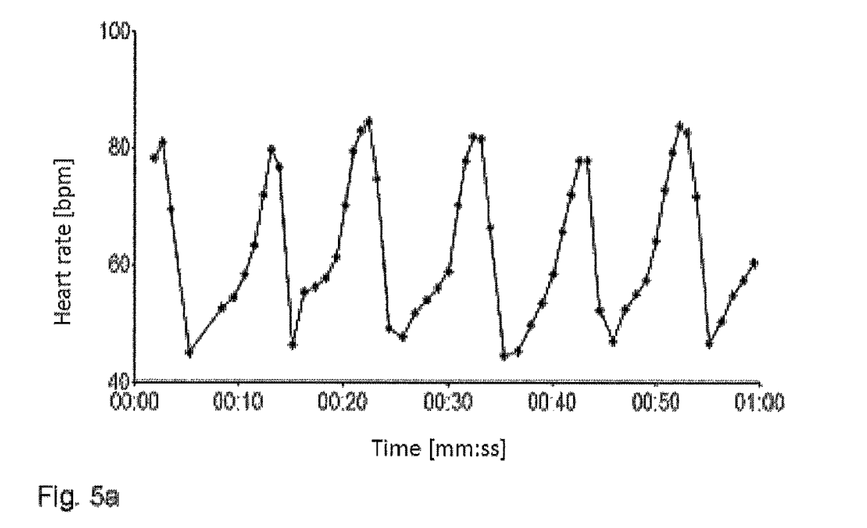
FIG. 5 shows two further heart-rate curves, which were measured on two different subjects.
Figure 5B:
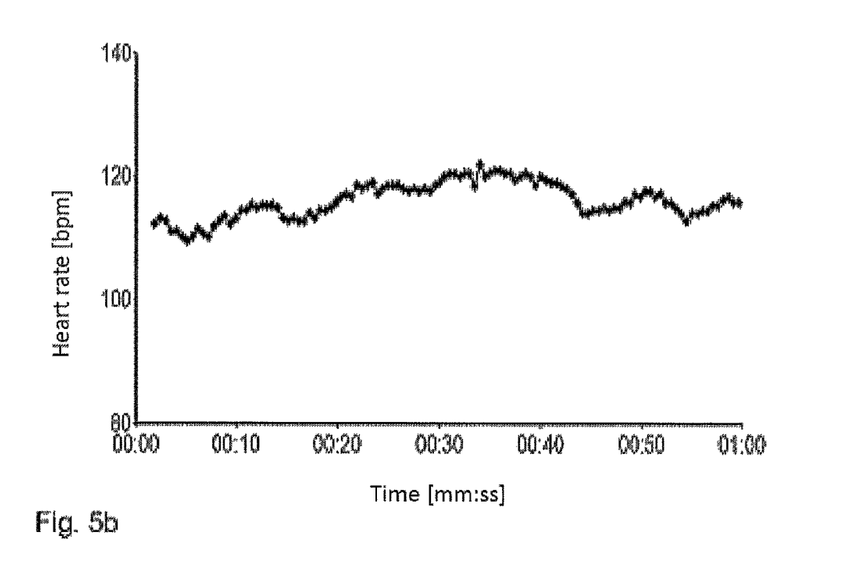
Figure 5C:
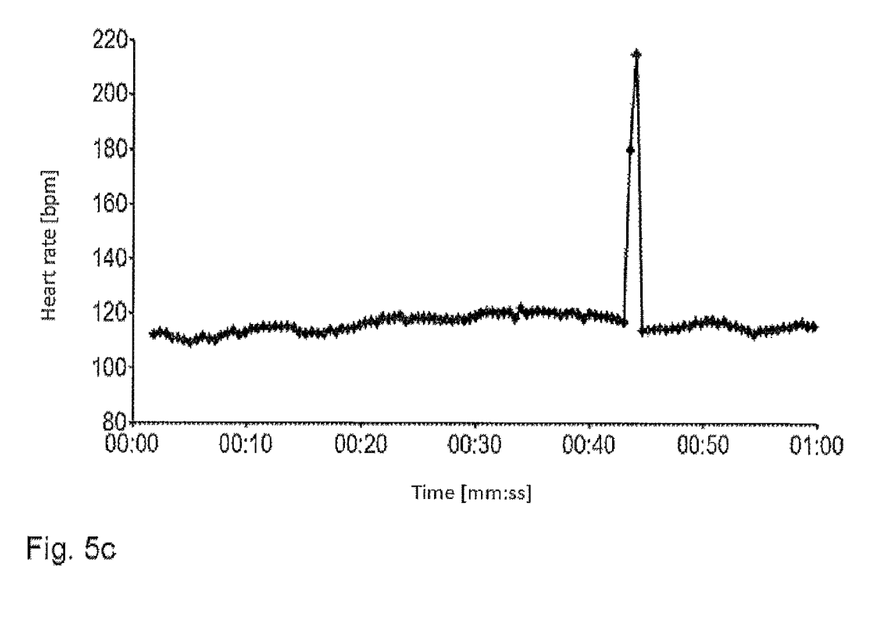

FIG. 5 shows two heart-rate curves measured on two different subjects (a, b). It is already obvious from the visual impression that curve a) comprises much larger fluctuations of the heart rates than does curve b). Correspondingly, the standard deviation S of the first curve is calculated as 8.84 bpm. The standard deviation S of the second curve amounts to only 2.88 bpm, as the manifestation of the greatly reduced range of fluctuation of the heart rate. Curve c) of FIG. 5 is identical with curve b), with the difference that the heart-rate variation contains a single artifact (defect) as an example. Artifacts can occur very easily during the measurement, for example if the subjects are moving or coughing. The resulting standard deviation S of the measurement c) amounts to 17.04 bpm and is therefore much greater than the standard deviation S of measurement a), even though measurement c) exhibits a very small fluctuation of the heart rate except for the artifact. This illustrates the need for a particularly careful handling with artifacts or a particularly careful removal of artifacts, in order to avoid false and misleading evaluations.

In order to eliminate the artifacts in the heart-rate curve, it is prior art to filter the heart-rate curve. Thus WO 2014/101913 A1 describes the filtering in the time domain, which in particular permits a sparingly computer-intensive data analysis. In the publication: "Filtering Poincaré plots" of Jaroslaw Piskorski and Przemyslaw Guzik (COMPUTATIONAL METHODS IN SCIENCE AND TECHNOLOGY 11(1), 39-48, 2005), a filtration technique is described that is based on the computer-assisted analysis of Poincaré diagrams. In a Poincaré diagram, each point on the heart-rate curve is plotted against the following point in an XY diagram. Poincaré diagrams, in which the X-coordinates correspond to the measured points of the heart-rate curve and the Y-coordinates are formed by the measured points of the heart-rate curve shifted by the index 1, can be generated simply from the heart-rate curve, and so they may be regarded here as an analysis in a phase domain. DE 10 2011 012 619 A1 also discloses the Poincaré plot for the analysis and for filtering of artifacts. The analysis in the phase domain or via the Poincaré diagram likewise permits the possibility of a sparingly computer-intensive data analysis.

Figure 6A:
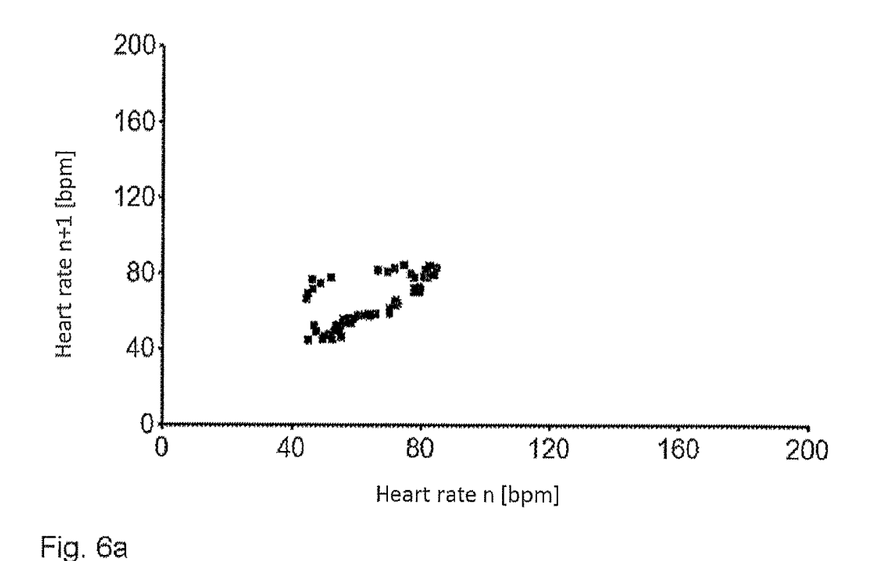
FIG. 6 shows the Poincaré diagrams associated with FIG. 5.
Figure 6B:
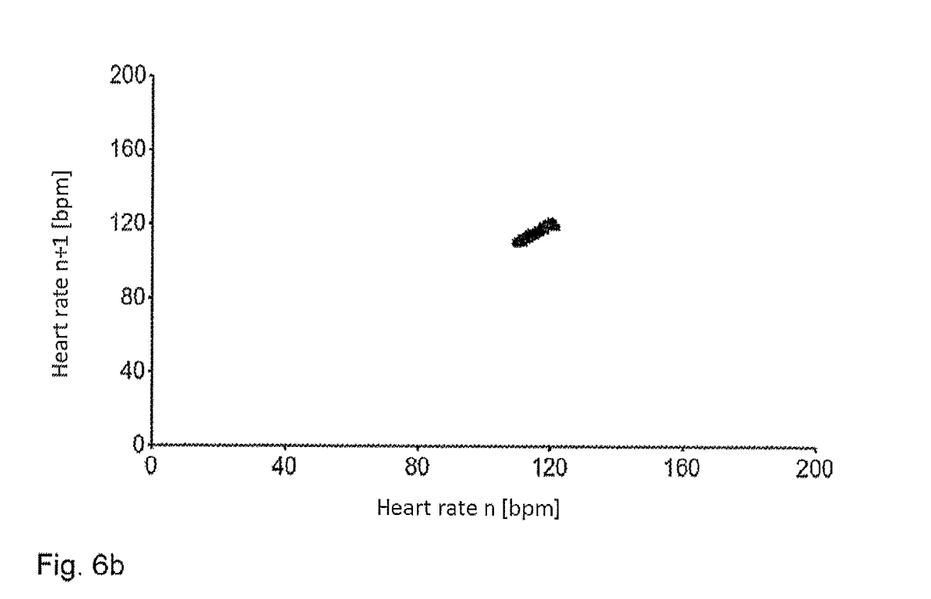
Figure 6C:
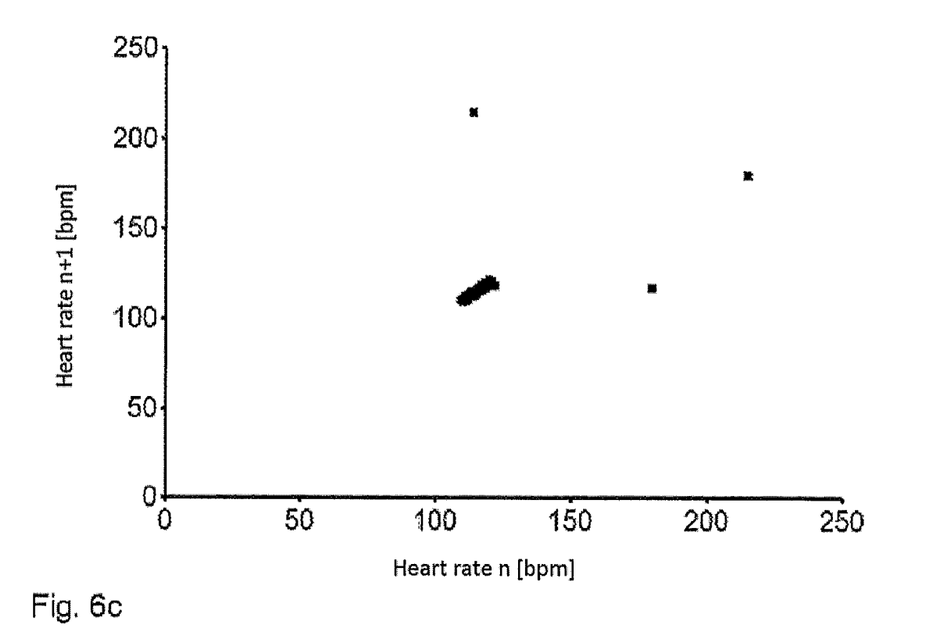

FIG. 6 shows the Poincaré diagram associated with FIG. 5. The artifacts in c) can be clearly recognized as outliers outside the point cloud. In this connection, it is immaterial whether the Poincaré diagram is constructed as a point cloud of the heart rates or as a point cloud of the time intervals, since both can be converted very easily into one another by mathematical transformation.

The LF/HF ratio mentioned in the prior art, as well as the ratios mentioned in DE 10 2006 039 957 A1 and EP 1 156 851 B1, correspond merely to a signal-to-noise ratio, wherein the amplitude of the respiratory sinus arrhythmia is used as the signal component and all other frequencies occurring outside the respiratory rate are treated as the noise component.

It is known from the literature that the LF/HF ratio correlates with the SD2/SD1 ratio, wherein the parameters SD2 and SD1 may be determined from the Poincaré diagram (Correlations between the Poincaré plot and conventional heart rate variability parameters assessed during paced breathing. Guzik P[1], Piskorski J, Krauze T, Schneider R, Wesseling K H, Wykretowicz A, Wysocki H., J Physiol Sci. 2007 February; 57(1):63-71. Epub 2007 Feb. 3). Therein it is stated, for example: "The LF/HF significantly correlated with SD2 and SD2/SD1 representing the balance between long- and short-term HRV".

Figure 3C:
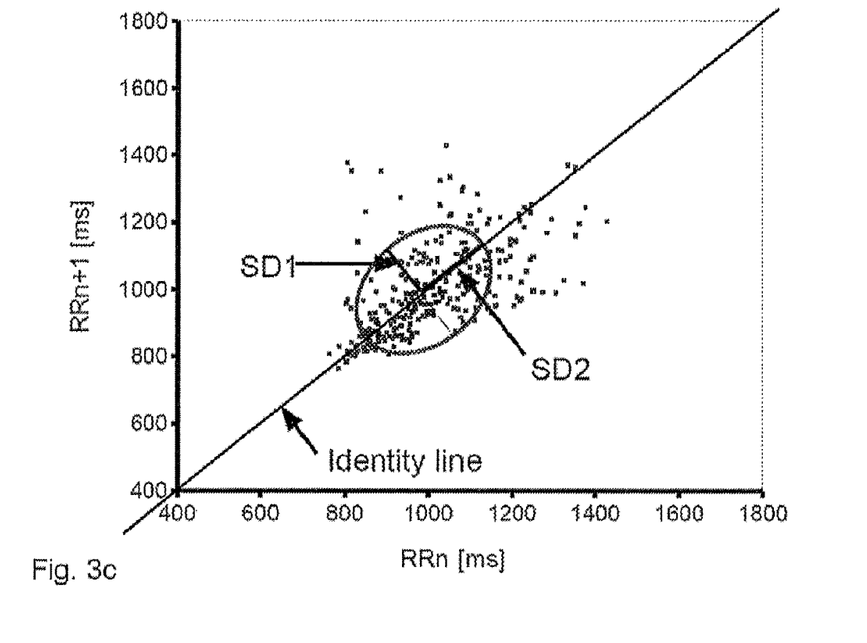

As already indicated in the foregoing, the Poincaré diagram represents the time-based correlation of successive heartbeats (RR interval) in an X-Y diagram. In this connection, the time elapsed in milliseconds between two heartbeats is denoted as the RR interval. Thus each RR interval is a function of the preceding RR interval. FIG. 3c shows a typical Poincaré diagram, calculated from the heart-rate curve shown in FIG. 3a. Each value pair (x; y) is obtained from the respective RR interval (X-value: $RR_n$) and its successor (Y-value: $RR_{n+1}$). The angle bisector (identity line) characterizes all RR intervals for which $RR_{n+1}=RR_n$ is valid. From the Poincaré diagram, it is now possible to determine the variables SD1 and SD2, where SD1 is the measure for the distribution of the measured points transverse to the identity line, for which purpose all points are projected onto a line that is oriented transverse to the identity line and their standard deviation is calculated, and wherein it is generally recognized that SD1 quantifies primarily the fast changes of the RR intervals; and that SD2 is the measure for the distribution of the measurement points along the identity line, for which purpose all points are projected onto the identity line and their standard deviation is calculated, and wherein it is generally recognized that SD2 quantifies primarily the slow changes of the RR intervals.

Since the graphical determination may absolutely be complex and necessitate corresponding computing power, an alternative calculation method, which is possible with much fewer computing steps, will be discussed in the following. It is prior art that the two parameters SD1 and SD2 can also be calculated in simple manner (Do existing measures of Poincaré plot geometry reflect nonlinear features of heart rate variability? Brennan M., Palaniswami M, Kamen P., IEEE Trans Biomed Eng. 2001 November; 48(11): 1342-7).

Thus fast changes of the heartbeat sequence can be represented via the RMSSD (root mean square of successive differences):

$$RMSSD = \sqrt{\frac{\sum_{n=1}^{N-1}(RR_{n+1}-RR_n)^2}{N-1}},$$

from which SD1 can then be derived:

$$SD1 = \frac{RMSSD}{\sqrt{2}}.$$

SD2 is obtained when, from the total dispersion SDDN $$SDNN = \sqrt{\frac{\sum_{n=1}^{N}(RR_n - RR_{mean})^2}{N-1}},$$

which ultimately represents a kind of standard deviation, in which mean value $$RR_{mean} = \frac{\sum_{n=1}^{N} RR_n}{N},$$

SD1 is appropriately subtracted:

$$SD2 = \sqrt{2 \times SDNN^2 - SD1^2}.$$

From the values obtained in this way for SD1 and SD2, it is then possible to form a signal-to-noise ratio $$G = \frac{SD2}{SD1}.$$

This signal-to-noise ratio G, however, is only permitted for determination of the respiratory sinus arrhythmia, as is needed, for example, for biofeedback purposes.

It is the task of the present invention to permit a more informative quantification in the phase domain.

The task of the invention is accomplished by a method and a device for quantification of a respiratory sinus arrhythmia as well as by the use of such a method or of such a device with the features of the independent claims. Further advantageous embodiments, which as the case may be are also independent thereof, can be found in the dependent claims as well as the following description.

In this connection, the invention proceeds from the basic knowledge that methods, which inherently permit more informative quantification during the analysis in the frequency domain, surprisingly are also advantageous in the phase domain. Thus, in the frequency domain, an interpolation is able to minimize harmonic artifacts that are caused by the time-related irregularity of the recorded measured values, while the selectivity can be increased by suitable coefficients or by a detrending. Surprisingly, these measures exhibit great advantages in the phase domain also or in the investigation of Poincare diagrams.

Thus an informative quantification can be obtained by a method for quantification of a respiratory sinus arrhythmia, in which firstly a heart-rate curve is measured and then the time elapsed $RR_n$ between two heartbeats is determined and, by an analysis of the time elapsed $RR_n$ between the heartbeats, the respiratory sinus arrhythmia is quantified from a ratio containing SD1 and SD2, when a value G', where $$G' = a\frac{SD2^b}{(SD1+c)^d}$$

is used for quantification. Likewise, a device for quantification of a respiratory sinus arrhythmia with means for measurement of a heart-rate curve and means for analysis of the heart-rate curve, wherein the quantification device comprises means for determination of the time elapsed $RR_n$ between two heartbeats and for calculation of a ratio containing SD1 and SD2, which is the basis for the quantification of the respiratory sinus arrhythmia, permits an informative quantification when it comprises means for output of a value G' as the quantification of the respiratory sinus arrhythmia, where $$G' = a\frac{SD2^b}{(SD1+c)^d},$$

Supplementarily, however, an informative quantification may also be obtained inherently even by a method for quantification of a respiratory sinus arrhythmia, in which firstly a heart-rate curve is measured and then the time elapsed $RR_n$ between two heartbeats is determined and, by an analysis of the time elapsed $RR_n$ between the heartbeats, the respiratory sinus arrhythmia is quantified from a ratio containing SD1 and SD2, when this method is characterized in that the heart-rate curve is interpolated before the calculation of the ratio containing SD1 and SD2. If a device for quantification of a respiratory sinus arrhythmia with means for measurement of a heart-rate curve and means for analysis of the heart-rate curve, wherein the quantification device comprises means for determination of the time elapsed $RR_n$ between two heartbeats and for calculation of a ratio containing SD1 and SD2, which is the basis for the quantification of the respiratory sinus arrhythmia, is characterized by means for interpolation of the heart-rate curve, an informative quantification of the respiratory sinus arrhythmia is accordingly likewise obtained. In this connection, it will be understood that, in the first place, it is immaterial how the ratio containing SD1 and SD2 is specifically calculated, since the corresponding advantages can be demonstrated for various types of quantification. Especially in the use of the values G or G' as ratios, highly informative quantifications are obtained by the interpolation.

Accumulatively or alternatively to the approaches described in the foregoing, an informative quantification may be obtained by a method for quantification of a respiratory sinus arrhythmia, in which firstly a heart-rate curve is measured and then the time elapsed $RR_n$ between two heartbeats is determined and, by an analysis of the time elapsed $RR_n$ between the heartbeats, the respiratory sinus arrhythmia is quantified from a ratio containing SD1 and SD2, when this method is characterized in that the heart-rate curve is detrended before the calculation of the ratio containing SD1 and SD2. In the present connection, the term "detrending" denotes the removal of a trend from the values that were inserted as basis for the calculation of the ratio containing SD1 and SD2. Accordingly, when a device for quantification of a respiratory sinus arrhythmia with means for measurement of a heart-rate curve and means for analysis of the heart-rate curve, wherein the quantification device comprises means for determination of the time elapsed $RR_n$ between two heartbeats and for calculation of a ratio containing SD1 and SD2, which is the basis for the quantification of the respiratory sinus arrhythmia, is characterized by means for detrending of the heart-rate curve, an informative quantification of the respiratory sinus, arrhythmia is likewise obtained. In the present connection, the term "detrending" accordingly denotes the removal of a trend from the values that were inserted as basis for the calculation of the ratio containing SD1 and SD2. In a first approach, it appears to be immaterial how the ratio containing SD1 and SD2 is specifically calculated, since the corresponding advantages can be demonstrated for various types of quantification. In particular, low-frequency artifacts can be removed in this way and the informativeness of the quantification increased toward lower frequencies. Especially in the use of the values G or G' as ratios, highly informative quantifications are obtained by the detrending. This is the case in particular in cooperation with an interpolation.

Of the coefficients a, b, c and d, one of the coefficients a, b or d should be not equal to 1 and/or the coefficient c should be not equal to 0.

The exact choice of the coefficients depends on the degree of quantification that is desired for the specific application situation.

Preferably, the coefficient a lies between 0.5 and 1.5, although it has been proved by experimental investigations that an informative quantification is possible without difficulty even at a coefficient of 1.

Preferably, the coefficient b lies between 2.4 and 3.3, wherein it has been proved by experimental considerations that the value should preferably lie between 2.5 and 3.2. Depending on specific embodiment, a coefficient between 2.8 and 3.3, especially between 2.9 and 3.2, is also suitable.

The coefficient c is preferably chosen between 4.0 and 10.0, wherein especially values between 5.0 and 9.0 have been experimentally deemed advantageous.

As regards the coefficient d, values between 2.8 and 4.2, preferably between 2.9 and 4.1, have proved to be advantageous. Depending on specific implementation, the values for the coefficient d may also lie between 3.5 and 4.2, preferably between 3.6 and 4.1.

The aforesaid limits of the coefficients are optimized in particular for calculations of G', in which SD1 and SD2 are summed over approximately one minute or less. It is conceivable that other coefficients would be more suitable over longer summation intervals; in particular, an adaptation of the coefficient a, for example a considerable increase, appears advantageous here.

By a suitable choice of the coefficients, which if necessary may be experimentally determined without difficulty from a number of known heart-rate curves and the desired degree of quantification, the behavior of the quantification method or of the corresponding quantification device may even be adapted if necessary to other quantification methods or devices that are already known from the prior art. This may be done recursively, for example, by a kind of learning process, wherein the coefficients are experimentally iterated until the result for the respective value corresponds to the desired result for given heart-rate curve. Hereby it is possible to simulate the behavior of very energy-intensive or computer-intensive quantification methods and devices, so that comparable quantifications can already be obtained in this way by means of the energy-saving or computer-time-saving analysis in the phase domain or in the Poincaré diagram or in spaces that correspond to Poincaré diagrams, even by using little energy or with low computing expense, short computing time or low computer power.

Corresponding adaptations may be made both on very energy-intensive or computer-intensive quantification methods and devices that operate with short measuring intervals, and on very energy-intensive or computer-intensive quantification methods and devices that operate with measuring intervals longer than one minute, wherein correspondingly other coefficients may then possibly seem suitable.

Preferably, the interpolation of the heart-rate curve takes place to a heart-rate curve that was recorded with regular time intervals. This method, known from the Fourier transformation, especially also the fast Fourier transform (FFT), is used there to prevent harmonic artifacts, which may arise due to the irregular time intervals of the recorded heart-rate curves in the frequency domain, or to minimize their effects. Surprisingly, precisely an appropriate interpolation also permits an excellent improvement of the quantification in the phase domain, which ultimately is subject inherently to completely different laws.

In this connection, it is conceivable, for example, to interpolate the heart-rate curve to 5 Hz or 4 Hz, which then accordingly corresponds to the generation of a synthetic heart-rate curve that is recorded with 5 Hz or with 4 Hz, i.e. at intervals of respectively 200 msec or of 250 msec. It will be understood that, depending on specific implementation, other regular time intervals may be selected even here, although interpolations to 5 Hz or to 4 Hz have proved advantageous in practice.

As regards the interpolation, it is possible in particular to use a linear interpolation, which in particular can be executed very rapidly, very simply and sparingly energy-intensively. Alternatively, for example, interpolations via cubic splines are conceivable. It will be likewise understood that other interpolation principles may also be applied in this connection.

The corresponding method or the device is suitable in particular for a biofeedback, in which a measurement and evaluation are undertaken in real time and the result of the evaluation is displayed in real time. A corresponding display may be undertaken, for example, by "Good" or "Bad", or else by a finer resolution.

It will be understood that the features of the approaches described in the foregoing or in the claims may also be combined as the case may be, in order to be able to implement the advantages correspondingly cumulatively.

Further advantages, objectives and properties of the present invention will be explained on the basis of following description of exemplary embodiments, which in particular are also illustrated in the attached drawing. In the drawing.

Table 1 shows an actual measurement of the RR intervals and the heart rate derived from them.

Table 2 shows an interpolation of the measurement according to Table 1 to a regular measurement.

Table 3 shows a set of coefficients applicable in practice.

In the interpolation according to Table 2, a specifically 5-Hz linear interpolation is employed. Alternatively, for example, a 4-Hz cubic spline interpolation may also be used.

In practice, it is possible, by linear interpolation of an actually recorded heart-rate curve, as is illustrated by way of example in Table 1, for example, as an actual measurement of the RR intervals and of the heart rate derived from them, to simulate a measurement that is made every 200 msec, as is then illustrated in Table 2.

Starting from this Table 2, a detrending may first be undertaken, in which, as illustrated by way of example in FIG. 2, determines a basic tendency—here a downward path of the curve—by calculation of a linear regression line and is then subtracted from the values of Table 2, in order that an analysis process, which in particular may result in the values G or G' as quantification, is then undertaken with these data in the phase domain. For the quantification, the coefficients indicated in Table 3 are suitable in particular for measurement intervals or for time windows, in which SD1 and SD2 are summed, of less than one minute. For other measurement intervals or time windows, other coefficients, which may be experimentally determined without difficulty, however, could be more advantageous as the case may be.

These values may then be defined and used as quantification of the respiratory sinus arrhythmia.

Such a quantification may take place in particular for a biofeedback, for example, in which corresponding measurements and evaluations are undertaken in real time and the result of the evaluation is correspondingly displayed in real time. Thus, for example, the values G and G' may be reinterpreted in a display as "good" or "bad". If necessary, a finer reinterpretation is obviously conceivable here.

Supplementarily to the undertaken interpolation, it is of advantage when the values G' are respectively used for the quantification.

In an experimental comparison, it has been proved that known quantification devices or methods as are described, for example, in DE 10 2006 039 957 A1, are simulated with the coefficients listed in Table 3, wherein the calculations of the values G or G' to be undertaken, including the interpolation and also the adjustment if necessary of the coefficients a, b, c and d, need substantially less energy and computing time, and so an implementation is possible without difficulty with smaller appliances or with appliances to which little computer power or little energy is available, or else with powerful instruments, which operate correspondingly faster.

TABLES

| Time [sec] | RR interval [ms] | Heart rate [bpm] |
| --- | --- | --- |
| 0 | 822 | 72.99 |
| 848 | 848 | 70.75 |
| 1754 | 906 | 66.23 |
| 2670 | 916 | 65.50 |
| 3618 | 948 | 63.29 |
| 4572 | 954 | 62.89 |
| 5490 | 918 | 65.36 |
| 6378 | 888 | 67.57 |
| 7240 | 862 | 69.61 |
| 8076 | 836 | 71.77 |
| 8888 | 812 | 73.89 |
| 9684 | 796 | 75.38 |
| 10492 | 808 | 74.26 |
| 11336 | 844 | 71.09 |
| 12222 | 886 | 67.72 |
| 13120 | 898 | 66.82 |
| 14042 | 922 | 65.08 |
| 14960 | 918 | 65.36 |
| 15856 | 896 | 66.96 |
| 16718 | 862 | 69.61 |
| 17562 | 844 | 71.09 |
| 18382 | 820 | 73.17 |
| 19184 | 802 | 74.81 |
| 19976 | 792 | 75.76 |
| 20784 | 808 | 74.26 |
| 21634 | 850 | 70.59 |
| 22524 | 890 | 67.42 |
| 23438 | 914 | 65.65 |
| 24366 | 928 | 64.66 |
| 25286 | 920 | 65.22 |
| 26184 | 898 | 66.82 |
| 27058 | 874 | 68.65 |

TABLE 2

| Time [sec] | RR interval [ms] | Heart rate [bpm] |
| --- | --- | --- |
| 0 | 822 | 72.99 |
| 200 | 828 | 72.46 |
| 400 | 834 | 71.94 |
| 600 | 840 | 71.43 |
| 800 | 847 | 70.84 |
| 1000 | 858 | 69.93 |
| 1200 | 871 | 68.89 |
| 1400 | 883 | 67.95 |
| 1600 | 896 | 66.96 |

TABLE 2-continued

| Time [sec] | RR interval [ms] | Heart rate [bpm] |
|---|---|---|
| 1800 | 907 | 66.15 |
| 2000 | 909 | 66.01 |
| 2200 | 911 | 65.86 |
| 2400 | 913 | 65.72 |
| 2600 | 915 | 65.57 |
| 2800 | 920 | 65.22 |
| 3000 | 927 | 64.72 |
| 3200 | 934 | 64.24 |
| 3400 | 941 | 63.76 |
| 3600 | 947 | 63.36 |
| 3800 | 949 | 63.22 |
| 4000 | 950 | 63.16 |
| 4200 | 952 | 63.03 |
| 4400 | 953 | 62.96 |
| 4600 | 953 | 62.96 |
| 4800 | 945 | 63.49 |
| 5000 | 937 | 64.03 |
| 5200 | 929 | 64.59 |
| 5400 | 922 | 65.08 |
| 5600 | 914 | 65.65 |
| 5800 | 908 | 66.08 |
| 6000 | 901 | 66.59 |
| 6200 | 894 | 67.11 |

TABLE 3

| a | b | c | d |
|---|---|---|---|
| 1 | 3.0640933514 | 6.1416416168 | 3.8932845592 |
| 1 | 2.9336259365 | 5.8386063576 | 3.705612421 |
| 1 | 2.9868226051 | 7.0778589249 | 3.6734967232 |
| 1 | 3.0965418816 | 8.7936115265 | 3.7033727169 |
| 1 | 2.8916110992 | 5.5824341774 | 3.6648161411 |
| 1 | 3.0149903297 | 5.5045495033 | 3.9051029682 |
| 1 | 3.0251405239 | 5.3571920395 | 3.9388401508 |
| 1 | 3.0995018482 | 5.3888492584 | 4.0623898506 |
| 1 | 3.1028745174 | 5.3845295906 | 4.0731034279 |
| 1 | 2.5600000000 | 6.2700000000 | 2.9600000000 |

The invention claimed is:

1. A quantification method for quantification of a respiratory sinus arrhythmia, in which firstly a heart-rate curve is measured and then a time elapsed $RR_n$ between two heartbeats is determined and, by an analysis of the time elapsed $RR_n$ between the heartbeats, the respiratory sinus arrhythmia is quantified from a ratio containing SD1 and SD2, wherein $$SD1 = \frac{RMSSD}{\sqrt{2}},$$

$$SD2 = \sqrt{2 \times SDNN^2 - SD1^2},$$

$$SDNN = \sqrt{\frac{\sum_{n=1}^{N}(RR_n - RR_{mean})^2}{N-1}},$$

$$RMSSD = \sqrt{\frac{\sum_{n=1}^{N-1}(RR_{n+1} - RR_n)^2}{N-1}} \text{ and}$$

$$RR_{mean} = \frac{\sum_{n=1}^{N} RR_n}{N},$$

wherein a value G', where $$G' = a\frac{SD2^b}{(SD1+c)^d}$$

is the quantification of the respiratory sinus arrhythmia;
wherein "a" lies between 0.5 and 1.5;
wherein "b" lies between 2.4 and 3.3;
wherein "c" lies between 4.0 and 10.0;
wherein "d" lies between 2.8 and 4.2;
wherein SD1 is a measure for the distribution of the measured points transverse to the identity line; and
wherein SD2 is a measure for the distribution of the measurement points along the identity line.

2. The quantification method according to claim 1, wherein the heart-rate curve is interpolated before the calculation of the ratio containing SD1 and SD2.

3. The quantification method according to claim 2, wherein the heart-rate curve is interpolated to a heart-rate curve recorded with regular time intervals.

4. The quantification method according to claim 1, wherein the heart-rate curve is detrended before the calculation of the ratio containing SD1 and SD2.

5. The quantification method according to claim 4, wherein the heart-rate curve is detrended by determination of a linear tendency of the heart-rate curve by calculation of a linear regression line and subtraction of the linear regression line from a linear interpolation of the heart-rate curve recorded with regular time intervals.

6. A method using the quantification method according to claim 1 for biofeedback, comprising:
undertaking a plurality of measurements and a plurality of evaluations of the the measurements; and
displaying results of the evaluations.

7. The quantification method according to claim 1, wherein "a" is 1.

8. The quantification method according to claim 1, wherein "b" lies between 2.5 and 3.2.

9. The quantification method according to claim 1, wherein "c" lies between 5.0 and 9.0.

10. The quantification method according to claim 1, wherein "d" lies between 2.9 and 4.1.

* * * * *